US010544071B2

(12) United States Patent
Senetar et al.

(10) Patent No.: US 10,544,071 B2
(45) Date of Patent: Jan. 28, 2020

(54) HEAT RECOVERY IN THE PROCESS OF PRODUCTION OF BUTADIENE

(71) Applicants: UOP LLC, Des Plaines, IL (US); TPC Group, LLC, Houston, TX (US)

(72) Inventors: John J. Senetar, Naperville, IL (US); Joseph G. Duff, League City, TX (US); Jillian M. Horn, Decatur, GA (US); Clifford A. Maat, Pearland, TX (US); Michael O. Nutt, Pearland, TX (US)

(73) Assignees: UOP LLC, Des Plains, IL (US); TPC Group LLC, Houston, TX (US)

( * ) Notice: Subject to any disclaimer, the term of this patent is extended or adjusted under 35 U.S.C. 154(b) by 0 days.

(21) Appl. No.: 15/968,914

(22) Filed: May 2, 2018

(65) Prior Publication Data
US 2018/0251412 A1 Sep. 6, 2018

Related U.S. Application Data

(63) Continuation of application No. PCT/US2016/060647, filed on Nov. 4, 2016.

(60) Provisional application No. 62/252,131, filed on Nov. 6, 2015.

(51) Int. Cl.
C07C 5/48 (2006.01)
C07C 5/42 (2006.01)
C07C 7/11 (2006.01)

(52) U.S. Cl.
CPC . *C07C 5/48* (2013.01); *C07C 7/11* (2013.01)

(58) Field of Classification Search
CPC .............. C07C 5/48; C07C 5/42; C07C 7/05
See application file for complete search history.

(56) References Cited

U.S. PATENT DOCUMENTS

| 3,557,238 | A | * | 1/1971 | Cunningham | ............ C07C 5/48 502/51 |
| 3,728,413 | A | | 4/1973 | Woerner | |
| 3,884,650 | A | | 5/1975 | Woerner | |
| 4,125,381 | A | | 11/1978 | Rogers | |
| 6,371,058 | B1 | | 4/2002 | Tung | |
| 7,323,147 | B2 | | 1/2008 | Lumgair, Jr. et al. | |

(Continued)

FOREIGN PATENT DOCUMENTS

| CN | 102826950 | 12/2012 |
| CN | 102875314 | 1/2013 |

(Continued)

OTHER PUBLICATIONS

International Search Report for PCT/US2016/060647, dated Feb. 27, 2017.
Written Opinion for PCT/US2016/060647, dated Feb. 27, 2017.

*Primary Examiner* — Youngsul Jeong
(74) *Attorney, Agent, or Firm* — Greer, Burns & Crain, Ltd.

(57) ABSTRACT

The process to recover heat in oxidative dehydrogenation of butene to butadiene is presented. The process utilizes heat recovered in oxidative dehydrogenation of butene to butadiene to generate steam. The process utilizes the circulated water stream generated in oxidative dehydrogenation of butene to butadiene for steam generation. A feedstream comprising butene is mixed with steam and preheated air at the inlet of the oxidative dehydrogenation reactor.

20 Claims, 1 Drawing Sheet

(56) References Cited

U.S. PATENT DOCUMENTS

2014/0200381 A1* 7/2014 Josch .................. C07C 7/05
                                                    585/621
2016/0023963 A1* 1/2016 Maat .................. C07C 5/48
                                                    585/329

FOREIGN PATENT DOCUMENTS

CN      103965001       8/2014
EP      1359989 A2      11/2003

* cited by examiner

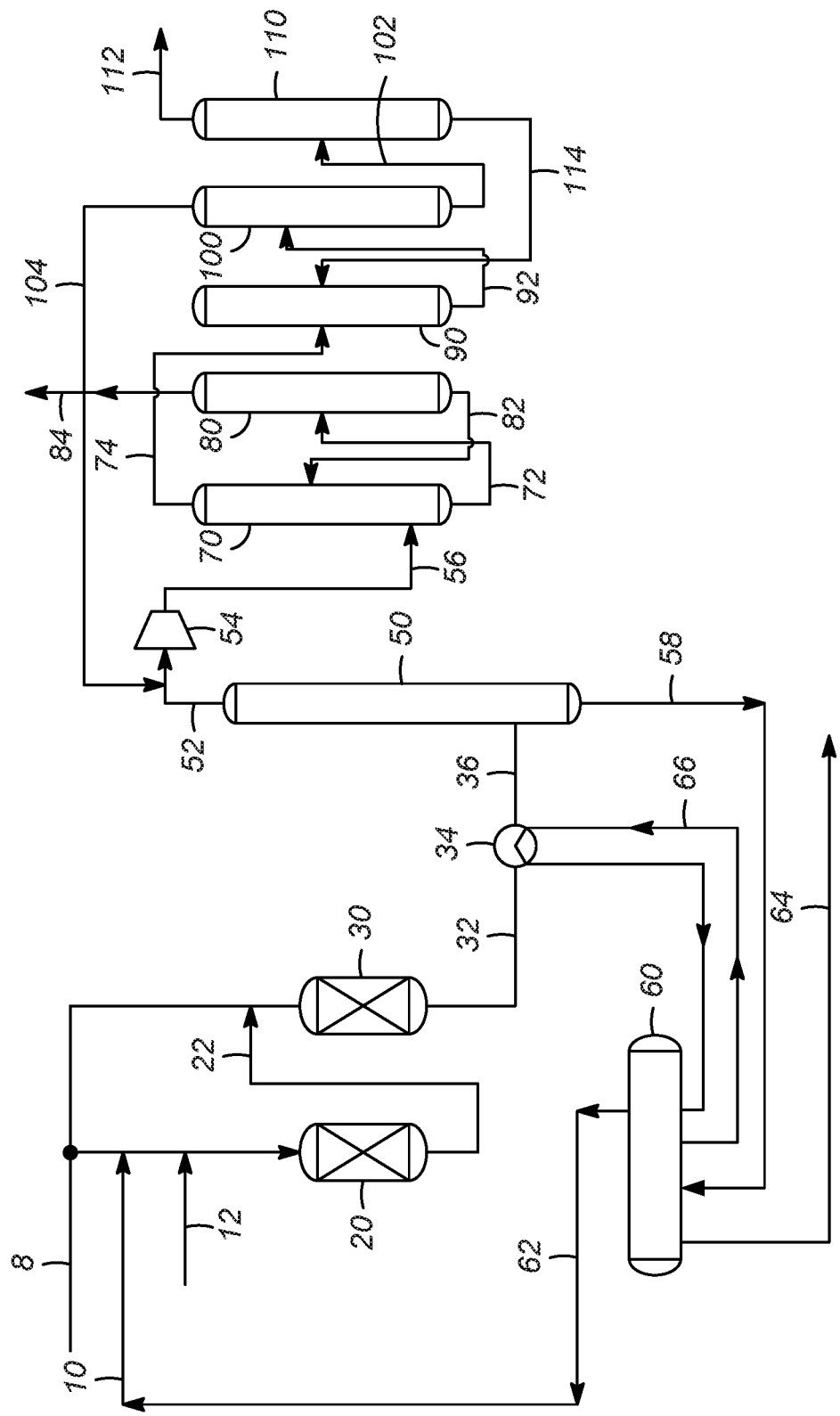

HEAT RECOVERY IN THE PROCESS OF PRODUCTION OF BUTADIENE

STATEMENT OF PRIORITY

This application is a continuation of co-pending International Application No. PCT/US2016/60647, entitled HEAT RECOVERY IN THE PROCESS OF PRODUCTION OF BUTADIENE, filed Nov. 4, 2016, which claims the benefit of U.S. Provisional Application No. 62/252,131 entitled HEAT RECOVERY IN THE PROCESS OF PRODUCTION OF BUTADIENE, filed Nov. 6, 2015, the contents of each of which is hereby incorporated by reference in its entirety.

FIELD OF THE INVENTION

The field of the subject matter is a process for heat recovery for steam generation in on-purpose butadiene production.

BACKGROUND

The production of on-purpose butadiene by oxidative dehydrogenation process requires a large amount of diluents. The on-purpose butadiene is a process that can convert n-butenes to butadiene. Conventionally, steam is used as a diluent to control the exothermic temperature rise in the reactor and provide dilution. This prevents undesired side reactions. The steam may be used to maintain catalyst activity. Typically, the molar ratio of steam to butene in the reactor ranges from 5 to 20. Also, water may be generated in addition to steam in the process of production of butadiene by oxidative dehydrogenation. The hydrogen atoms removed in the reaction are converted to water by addition of air or oxygen enriched stream.

The combined steam fed to the process and the steam generated during the process need to be removed from the product for recovery and purification of the butadiene product. Generally, the steam is removed as water by condensation. But, any heavy hydrocarbons and oxygenates in the reactor effluent will also be condensed along with steam and the water that leaves the reactor includes heavy hydrocarbons and oxygenates.

The water balance for the process favors the recycling of the condensed water to generate steam required for the reactor. Conventionally, an evaporator is used to generate steam from the condensed water. The hydrocarbons that are not evaporated for a hydrocarbon layer on top of the evaporated water and eventually grow with time. This results in fouling of the heat exchange surface in the boiler, high temperature, and potential slugs of the vaporized hydrocarbon.

Therefore, there is need for an improved process for energy efficiency and heat recovery in the oxidative dehydrogenation process. In addition, there is a need for an improved process for steam generation from the water generated in oxidative dehydrogenation reaction that can overcome the above mentioned problems and undesired side reactions.

SUMMARY

An embodiment of the invention is a process for heat recovery in oxidative dehydrogenation of butene to butadiene comprising passing a feedstream comprising butene along with steam and preheated air to an oxidative dehydrogenation reactor. The feedstream is oxidatively dehydrogenated over a dehydrogenation catalyst in the oxidative dehydrogenation reactor to form a product stream comprising butadiene. The product stream from the dehydrogenation reactor is subsequently passed to a heat exchanger to cool the stream. The cooled stream is passed to a quench tower to generate a cooled stream with reduced water, and a condensed water stream. The generated water stream is subsequently passed to a disengaging drum to generate steam, a circulated water stream and a draw-off stream.

Another embodiment of the invention is a process for steam generation by heat recovery in oxidative dehydrogenation of butene to butadiene comprising passing a feedstream comprising butene along with steam and preheated air to an oxidative dehydrogenation reactor. The feedstream is oxidatively dehydrogenated over a dehydrogenation catalyst in the oxidative dehydrogenation reactor to form a product stream. The product stream from the dehydrogenation reactor is subsequently passed to a quench tower to generate a cooled product stream and a water stream. The generated water stream is subsequently passed to a disengaging drum to generate steam, a circulated water stream and a draw-off stream comprising hydrocarbons and oxygenates. The draw-off stream is removed in the disengaging drum. The generated steam is passed to the oxidative dehydrogenation reactor.

The present invention seeks to provide a streamlined process to generate steam by heat recovery in oxidative dehydrogenation of butene to butadiene. It is an advantage of the invention to recover of steam from the circulated water using a disengaging drum for disengagement and removal of any hydrocarbon layer. These and other features, aspects, and advantages of the present invention will become better understood upon consideration of the following detailed description, drawings and appended claims.

BRIEF DESCRIPTION OF THE DRAWING

FIG. 1 is a flow scheme for the process of the present invention.

DETAILED DESCRIPTION

The dehydrogenation of butene to butadiene requires a large amount of diluent steam. Traditionally, the steam is produced in dehydrogenation processes of butene or butane to butadiene by condensing water using an evaporator. A drawback of this conventional method is that heavy hydrocarbons are not evaporated and form a hydrocarbon layer on top of evaporating water and eventually cause fouling of the heat exchange surface in the boiler and potential slugs of vaporized hydrocarbon.

The present subject matter provides a method of heat recovery in dehydrogenation of butene to butadiene by passing water to a drum to generate steam and a circulated water stream. Conventionally, a boiler is used to generate the steam. The present subject matter advantageously provides a disengaging drum to generate steam and a circulating water stream that can be used to generate steam by natural convection. The use of disengaging drum prevents the build-up of heavy hydrocarbon layer and removal of any hydrocarbon layer from the drum. Therefore, the present subject matter beneficially provides prevention of any fouling in downstream processing. An additional benefit of the present subject matter is water management, which can be a very expensive process in any chemical plant or a refinery. The prevention of any carryover of fouling by the hydrocarbon downstream can be accomplished by incomplete or partial vaporization of water in the water management system.

A general understanding of the process for selectively heat recovery in oxidative dehydrogenation of butene to butadiene can be obtained by reference to the FIGURE. The FIGURE has been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

The present invention, as shown in the FIGURE, includes passing a feedstream in line 12 comprising butene along with steam in line 10 and air in line 8 to a first dehydrogenation reactor unit 20. The air is rich in oxygen and serves as potential oxygen source. The steam in line 10 may be superheated before it is passed to the first dehydrogenation reactor unit 20. The dehydrogenation reactor units 20, 30 comprise a catalyst, and are operated at dehydrogenation reaction conditions to generate an effluent stream in line 32. The air in line 8 may be preheated before passing it to the dehydrogenation reactor 20. The mixture comprising feedstream in line 12 and steam in line 10 may be superheated to a temperature of at least 205° C. before passing the mixture to the dehydrogenation reactor unit 20.

The dehydrogenation reactor may be a two stage reactor including the first dehydrogenation reactor 20 and a second dehydrogenation reactor 30. An intermediate stream 22 may be taken from the first dehydrogenation reactor 20 and is passed to the second dehydrogenation reactor 30. The intermediate steam 22 may be heat exchanged with the steam in line 10 before it is passed to the second dehydrogenation reactor 30.

The reactor units may be arranged in a series format, and can be positioned in any convenient manner, in particular in a manner that facilitates the transfer of reactants between reactor units, and provides for access to admit flows or withdraw process streams.

The present invention can utilize fixed bed reactors or moving bed reactors. A preferred mode is for the use of moving bed reactors, with fresh catalyst passed to the first reactor unit. The catalyst from the first reactor may be passed to the second reactor. The process can further include reactor units which comprise a plurality of reactor beds.

Operating conditions for the preferred dehydrogenation zone, comprising the dehydrogenation reactor units, of this invention will usually include an operating temperature in the range of from 500° C. to 700° C., an operating pressure from 100 to 450 kPa (absolute) and a liquid hourly space velocity of from about 0.5 to about 50 for each catalyst bed. The preferred operating temperature will be within the range of from about 540° C. to 660° C., and the preferred operating pressure is 100 to 250 kPa (absolute). A more preferred operating conditions include a temperature is 580° C. to 645° C., an operating pressure from 100 to 170 kPa (absolute), and preferably operating conditions such that the effluent stream from each reactor unit is at a temperature of above 500° C., and most preferably at 580° C., with an operating temperature between 600° C. to 645° C. The temperature can be controlled by the flow of steam to the reactor units. When the effluent stream temperature is too high, the steam can be used as a quench to bring the inlet temperature of the feed and oxidant to the next reactor to below 580° C.

The preferred dehydrogenation catalyst is comprised of a Group VIII metal, and preferably a platinum group component, preferably platinum, a tin component and an alkali metal component with a porous inorganic carrier material. Another metal that can be used is chromium. Other catalytic compositions may be used within this zone if desired. The preferred catalyst contains an alkali metal component chosen from cesium, rubidium, potassium, sodium and lithium. The preferred alkali metal is normally chosen from cesium and potassium. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions are available in patents, such as those cited above, and other standard references (U.S. Pat. Nos. 4,486,547 and 4,438,288).

The feed stream comprising butene is oxidatively dehydrogenated over the dehydrogenation catalyst to produce a product stream comprising butadiene in line 32. The product stream in line 32 from the dehydrogenation reactor is passed to a heat exchanger 34 to cool the stream. The cooled stream in line 36 from the heat exchanger is passed to a quench tower 50 to generate a cooled stream with reduced water in line 52 and a condensed water stream in line 58. The quench tower 50 is in downstream communication with the dehydrogenation reactor 30. The water stream from quench tower in removed from the bottom of the quench tower in line 58 and is passed to a disengaging drum 60 to generate steam in line 62, a circulating water stream in line 66 and a draw-off stream in line 64. The draw-off stream is removed from the disengaging drum in line 64. The draw-off stream comprises hydrocarbons and oxygenates. The disengaging drum 60 is in downstream communication with the dehydrogenation reactor 30.

The steam in line 62 is passed from the disengaging drum 60 to the dehydrogenation reactor 20. The steam in line 62 may be combined with the inlet steam in line 10 to the dehydrogenation reactor 20. The product stream comprising butadiene in line 32 may be cooled with water in line 66 from the disengaging drum 60. The heat exchanger 34 may be used to vaporize a portion of the circulating water stream in line 66 to generate steam. A portion of the water is vaporized on each pass of water from the quench tower to the disengaging drum. The product stream in line 32 may be used to partially vaporize the circulating water stream in line 66 by heat exchange before the circulating water stream is passed to the quench tower 50.

The product stream comprising butadiene and reduced water exits from the top of quench tower in line 52. The product stream in line 52 is passed to a compressor 54 to compress the product stream. The product stream may be compressed to about 1100 kPa to 1200 kPa. The compressed product stream in line 56 is passed to an oxygenate scrubber 70 to generate a scrubbed stream in line 72. The oxygenate scrubber 70 is in downstream communication with the quench tower 50. The reaction product in line 74 from the overhead of the oxygenate scrubber 70 is passed to the bottom of a C4 absorber 90. The scrubbed stream in line 72 from the bottom of the oxygenate scrubber 70 is passed to an oxygenate stripper 80 to generate a stripped stream in line 82 and a vapor stream in line 84. The gases in the vapor stream in line 84 are vented out. The oxygenate stripper is in downstream communication with the oxygenate scrubber 70. The C4 absorber 90 is in downstream communication with the oxygenate scrubber 70.

The stripped stream in line 82 from the bottom of the oxygenate stripper 80 is passed to the oxygenate scrubber 70. The reaction product in line 74 from the overhead of the oxygenate scrubber may be passed along with an absorption oil stream to the C4 absorber 90 to generate an absorption stream comprising butadiene in line 92. The C4 absorber 90 is in downstream communication with the oxygenate stripper 80. The butadiene and the C4 compounds are absorbed into the absorption oil stream. The absorption stream in line 92 is passed to a degasser tower 100 to remove non-C4 volatiles and generate a degassed stream in line 102. The overhead gas stream in line 104 from the degasser tower 100 may be passed to combine with product comprising butadiene in line 52 to be compressed by the compressor 54. The degasser tower 100 is in downstream communication with the C4 absorber 90. The degassed stream in line 102 is passed from the degasser tower is passed to a C4 stripper 110 to generate a crude butadiene product that is removed in line 112 from the C4 stripper. The C4 compounds including the butadiene are desorbed from the absorption oil under reduced pressure. The absorption stream is removed at the bottom of the C4 stripper in line 114 and is passed to the C4 absorber 90. The C4 stripper 110 is in downstream communication with the degasser tower 100.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for heat recovery in oxidative dehydrogenation of butene to butadiene comprising passing a feedstream comprising butene along with steam and preheated air to an oxidative dehydrogenation reactor; oxidatively dehydrogenating the feedstream over a dehydrogenation catalyst in the oxidative dehydrogenation reactor to form a product stream comprising butadiene; passing the product stream from the oxidative dehydrogenation reactor to a heat exchanger to cool the stream; passing the cooled stream to a quench tower to generate a cooled stream with reduced water, and a condensed water stream; and passing the water stream to a disenagaging drum to generate steam, a circulated water stream, and a draw-off stream. An embodiment of the invention is one, any or all of prior embodiments in this paragraph up through the first embodiment in this paragraph further comprising passing the generated steam from the disengaging drum to the oxidative dehydrogenation reactor. An embodiment of the invention is one, any or all of prior embodiments in this paragraph up through the first embodiment in this paragraph further comprising mixing the feedstream comprising butene with the steam and superheating the mixture to a temperature of at least 205° C. An embodiment of the invention is one, any or all of prior embodiments in this paragraph up through the first embodiment in this paragraph wherein the product stream is cooled with water from the disengaging drum. An embodiment of the invention is one, any or all of prior embodiments in this paragraph up through the first embodiment in this paragraph further comprising passing the product stream to the heat exchanger to vaporize a portion of the circulated water stream and generate steam. An embodiment of the invention is one, any or all of prior embodiments in this paragraph up through the first embodiment in this paragraph wherein the circulated water stream is partially vaporized by heat exchange with the product stream comprising butadiene. An embodiment of the invention is one, any or all of prior embodiments in this paragraph up through the first embodiment in this paragraph wherein the oxidative dehydrogenation reactor is a two stage reactor with the first stage generating an intermediate stream and passing the intermediate stream to the second stage, further comprising heat exchanging the steam with the intermediate stream. An embodiment of the invention is one, any or all of prior embodiments in this paragraph up through the first embodiment in this paragraph further comprising superheating the steam. An embodiment of the invention is one, any or all of prior embodiments in this paragraph up through the first embodiment in this paragraph further comprising passing the superheated steam to the oxidative dehydrogenation reactor. An embodiment of the invention is one, any or all of prior embodiments in this paragraph up through the first embodiment in this paragraph further comprising passing the product stream comprising butadiene to an oxygenate scrubber to generate a scrubbed stream. An embodiment of the invention is one, any or all of prior embodiments in this paragraph up through the first embodiment in this paragraph further comprising passing the scrubbed stream to oxygenate stripper to generate a stripped stream and a vapor stream. An embodiment of the invention is one, any or all of prior embodiments in this paragraph up through the first embodiment in this paragraph further comprising passing the stripped stream and an absorption oil to a C4 absorber to generate an absorption stream. An embodiment of the invention is one, any or all of prior embodiments in this paragraph up through the first embodiment in this paragraph further comprising passing the absorption stream to a degasser tower to remove non-C4 volatiles and generate a degassed stream. An embodiment of the invention is one, any or all of prior embodiments in this paragraph up through the first embodiment in this paragraph further comprising passing the degassed stream to a C4 stripper to generate a crude butadiene stream.

A second embodiment of the invention is a process for steam generation by heat recovery in oxidative dehydrogenation of butene to butadiene comprising passing a feedstream comprising butene along with steam and preheated air to an oxidative dehydrogenation reactor; oxidatively dehydrogenating the feedstream over a dehydrogenation catalyst in the oxidative dehydrogenation reactor to form a product stream; passing the product stream to a quench tower to generate a cooled product stream and a water stream; passing the water stream to a disengaging drum to generate steam, a circulating water stream, and a draw-off stream comprising hydrocarbons and oxygenates; removing the draw-off stream in the disengaging drum; and passing the steam to the oxidative dehydrogenation reactor An embodiment of the invention is one, any or all of prior embodiments in this paragraph up through the second embodiment in this paragraph further comprising mixing the feedstream comprising butene with the steam and superheating the mixture to a temperature of at least 205° C. An embodiment of the invention is one, any or all of prior embodiments in this paragraph up through the second embodiment in this paragraph further comprising heat exchanging the circulating water stream with the product stream before passing the product stream to the quench tower to vaporize a portion of the circulating water stream. An embodiment of the invention is one, any or all of prior embodiments in this paragraph up through the second embodiment in this paragraph further comprising passing the cooled product stream to a compressor, an oxygenate scrubber, and an oxygenate stripper to generate a scrubbed stream and the scrubbed stream to a C4 absorber to generate an absorption stream. An embodiment of the invention is one, any or all of prior embodiments in this paragraph up through the second embodiment in this paragraph further comprising passing the absorption stream to a degasser tower to remove non-C4 volatiles to generate a degassed stream. An embodiment of the invention is one, any or all of prior embodiments in this paragraph up through the second embodiment in this paragraph further comprising passing the degassed stream to a C4 stripper to generate a crude butadiene stream.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

What is claimed is:

1. A process for heat recovery in oxidative dehydrogenation of butene to butadiene comprising:
    passing a feedstream comprising butene along with steam and preheated air to an oxidative dehydrogenation reactor;
    oxidatively dehydrogenating the feedstream over a dehydrogenation catalyst in the oxidative dehydrogenation reactor to form a product stream comprising butadiene;
    passing the product stream from the oxidative dehydrogenation reactor to a heat exchanger to cool the product stream to produce a cooled product stream;
    passing the cooled product stream to a quench tower to generate a cooled stream with reduced water, and a condensed water stream; and
    passing the condensed water stream to a disengaging drum to generate a steam stream, a circulating water stream, and a separate draw-off stream comprising hydrocarbons and oxygenates.

2. The process of claim 1 further comprising passing the generated steam from the disengaging drum to the oxidative dehydrogenation reactor.

3. The process of claim 1 further comprising mixing the feedstream comprising butene with the steam to obtain a mixture and superheating the mixture to a temperature of at least 205° C.

4. The process of claim 1 wherein the product stream is cooled with the circulating water stream obtained from the disengaging drum.

5. The process of claim 1 further comprising passing the circulating water stream to the heat exchanger to vaporize a portion of the circulating water stream and generate steam.

6. The process of claim 4 wherein the circulating water stream is partially vaporized by heat exchange with the product stream comprising butadiene.

7. The process of claim 1 wherein the oxidative dehydrogenation reactor is a two stage reactor with the first stage generating an intermediate stream and passing the intermediate stream to the second stage, further comprising heat exchanging the generated steam stream with the intermediate stream.

8. The process of claim 1 further comprising superheating the generated steam stream to produce a superheated steam.

9. The process of claim 8 further comprising passing the superheated steam to the oxidative dehydrogenation reactor.

10. The process of claim 9 further comprising passing the product stream comprising butadiene to an oxygenate scrubber to generate a scrubbed stream.

11. The process of claim 10 further comprising passing the scrubbed stream to oxygenate stripper to generate a stripped stream and a vapor stream.

12. The process of claim 11 further comprising passing the stripped stream and an absorption oil to a C4 absorber to generate an absorption stream.

13. The process of claim 12 further comprising passing the absorption stream to a degasser tower to remove non-C4 volatiles and generate a degassed stream.

14. The process of claim 13 further comprising passing the degassed stream to a C4 stripper to generate a crude butadiene stream.

15. A process for steam generation by heat recovery in oxidative dehydrogenation of butene to butadiene comprising:
    passing a feedstream comprising butene along with steam and preheated air to an oxidative dehydrogenation reactor;
    oxidatively dehydrogenating the feed stream over a dehydrogenation catalyst in the oxidative dehydrogenation reactor to form a product stream;
    passing the product stream to a quench tower to generate cooled product stream and a water stream;
    passing the water stream to a disengaging drum to generate a steam stream, a circulating water stream, and a separate draw-off stream comprising hydrocarbons and oxygenates;
    removing the draw-off stream from the disengaging drum; and
    passing the generated steam stream to the oxidative dehydrogenation reactor.

16. The process of claim 15 further comprising mixing the feedstream comprising butene with the steam to obtain a mixture and superheating the mixture to a temperature of at least 205° C.

17. The process of claim 15 further comprising heat exchanging the circulating water stream with the product stream before passing the product stream to the quench tower to vaporize a portion of the circulating water stream.

18. The process of claim 17 further comprising passing the cooled product stream to a compressor, an oxygenate scrubber, and an oxygenate stripper to generate a scrubbed stream, and the scrubbed stream to a C4 absorber to generate an absorption stream.

19. The process of claim 18 further comprising passing the absorption stream to a degasser tower to remove non-C4 volatiles to generate a degassed stream.

20. The process of claim 19 further comprising passing the degassed stream to a C4 stripper to generate a crude butadiene stream.

* * * * *